US006453004B1

(12) United States Patent
Albeniz et al.

(10) Patent No.: US 6,453,004 B1
(45) Date of Patent: Sep. 17, 2002

(54) RADIOLOGY SYSTEM WITH DATA TRANSMISSION AND ASSOCIATED METHOD

(75) Inventors: Juan Albeniz, Paris; Alain Beauregard-Maronneau, Meulan; Andrej Dvorak, Paris; Jean Herzog, Sceaux; Thierry Salmon-Legagneur, Paris; Romuald Simmoneau, Jouy en Josas; Medhi Venon, Vouzon, all of (FR)

(73) Assignee: GE Medical Systems SA (FR)

( * ) Notice: Subject to any disclaimer, the term of this patent is extended or adjusted under 35 U.S.C. 154(b) by 0 days.

(21) Appl. No.: 09/585,478

(22) Filed: Jun. 1, 2000

(30) Foreign Application Priority Data

Jun. 4, 1999 (FR) .............................. 99 07108

(51) Int. Cl.[7] .......................... G01N 23/04; A61B 6/03
(52) U.S. Cl. ................................ 378/62; 378/4
(58) Field of Search ............................. 378/4, 62, 65, 378/901

(56) References Cited

U.S. PATENT DOCUMENTS 5,099,436 A  3/1992  McCown et al. ............ 364/550
6,035,328 A  * 3/2000  Soukal ........................ 600/300
6,101,407 A  * 8/2000  Groezinger .................. 128/922
6,359,961 B1 * 3/2002  Aufrichtig et al. ............ 378/41
2002/0004798 A1 * 1/2002  Babula et al. ........... 707/104.1

FOREIGN PATENT DOCUMENTS

WO       9816903       4/1998

OTHER PUBLICATIONS

IBM Research Disclosure,"Virtual URLs for Browsing and Searching Large Information Spaces", vol. 42, No. 413, Sep. 1998.

* cited by examiner

Primary Examiner—David V. Bruce
(74) Attorney, Agent, or Firm—Jay L. Chaskin

(57) ABSTRACT

Radiology system and method for data transmission comprising emission of an X-ray beam, reception of the X-ray beam after it has crossed an organ to be studied, reception control, an image former, a first network server associated with the reception control and a second network server associated with the image former, each server being capable of transmitting data in html format to a remote computer.

30 Claims, 4 Drawing Sheets

RADIOLOGY SYSTEM WITH DATA TRANSMISSION AND ASSOCIATED METHOD

CROSS-REFERENCE TO RELATED APPLICATIONS

This application claims the benefit of a priority under 35 USC 119 to French Patent Application No. 99 07108 filed Jun. 4, 1999.

BACKGROUND OF THE INVENTION

This invention concerns the field of X-ray apparatuses equipped with remote data transmission means.

An X-ray apparatus used, for example, for mammography, RAD or RF conventional radiology, neurological or even vascular (peripheral or cardiac) radiology generally consists:

- of an X-ray tube and a collimator in order to form and delimit an X-ray beam,
- of an image receiver, generally an X-ray image intensifier and a video camera, or even a solid state detector,
- of a positioner bearing the X-ray tube and collimator assembly, on one side, and image receiver, on the other, mobile in the space around one or more axes, and
- of a means of positioning the table, such as a table platform designed to support it in extended position.

The X-ray apparatus further comprises means of control of the X-ray tube, making it possible to adjust parameters such as dose, exposure time, high voltage, etc., and a means of control of the different motors enabling the X-ray apparatus to be moved on its different axes, as well as means of positioning the patient and means of image processing making possible a screen display and a storage of data for two- or three-dimensional images with functions such as a zoom, a translation along one or more perpendicular axes, a rotation on different axes, a subtraction of images or even an extraction of the contour. Those functions are assured by electronic cards that can undergo different adjustments.

Thus, upon installation, it is necessary to configure different parameters of the X-ray apparatus as a function of users' demand. A calibration must then be carried out to verify the accuracy of the indications supplied by the different sensors provided, for example, for measurement of high voltage, current, position or displacement of moving parts, image brightness, etc. Finally, in the course of use of the X-ray apparatus, it is necessary to undertake regular maintenance operations depending on errors produced, failures or the possible drift of certain components of the apparatus. Those operations are performed by a technician who comes to the site and carries out the required operations depending on the user's remarks and indications supplied by the apparatus, which can be provided with a memory space in which information on the different errors occurring in the apparatus is stored automatically.

Thus, depending on the type of error having occurred, the technician can deduce therefrom the component or component part having caused the error. He must then search for the component or component part to be replaced and install it in the X-ray apparatus.

BRIEF SUMMARY OF THE INVENTION

This invention provides an improved system for a rapid and economical communication of data from an X-ray system to a remote computer.

The X-ray system comprises a means of emission of an X-ray beam, a means of reception of the X-ray beam after it has crossed an organ to be studied, a reception control means, an image-forming means, a first network server associated with the reception control means and a second network server associated with the image-forming means, each server being capable of transmitting data in html format to a remote computer.

The image-forming means preferably comprises a computer storing in memory a document relating to errors that can occur in the system, the computer being provided with a screen and a graphics interface and capable of displaying on the screen at least one page containing a list of errors having occurred in the system with hyperlinks to the document.

In an embodiment of the invention, the system comprises a remote computer capable of receiving data in html format from the servers, said remote computer storing in memory a document relating to errors that can occur in the system and the computer being provided with a screen and a graphics interface and capable of displaying on the screen at least one page containing a list of errors having occurred in the system with hyperlinks to the document.

The document can contain, for each type of error, at least one test to be carried out in order to determine its cause.

The remote computer is advantageously capable of showing the page displayed by the computer of the image-forming means.

In an embodiment of the invention, the system includes at least one accessory connected to the image-forming means and capable of transmitting data to the remote computer through the image-forming means and the associated server.

The data in html format transmitted by the server associated with the reception control means to the remote computer advantageously passes through the image-forming means and the associated server. The data only undergo the processing necessitated by the passage through the image-forming means and associated server.

In an embodiment of the invention, the system contains diagnostic means loaded with errors that can occur in the system, the means being capable of diagnosing given errors selected according to their occurrence probability, the trouble they are likely to cause the user and the difficulty of using the corresponding diagnosis.

The invention also concerns a method of data transmission from an X-ray system, containing a means of emission of an X-ray beam, a means of reception of the X-ray beam after it has crossed an organ to be studied, a reception control means and an image-forming means, in which method data are transmitted in html format to a remote computer from a first network server associated with the reception control means and from a second network server associated with the image-forming means.

This invention will be better understood by studying the detailed description of an embodiment taken by way of nonlimitative example and illustrated by the attached drawings, on which:

DETAILED DESCRIPTION OF THE INVENTION

Figure 1:
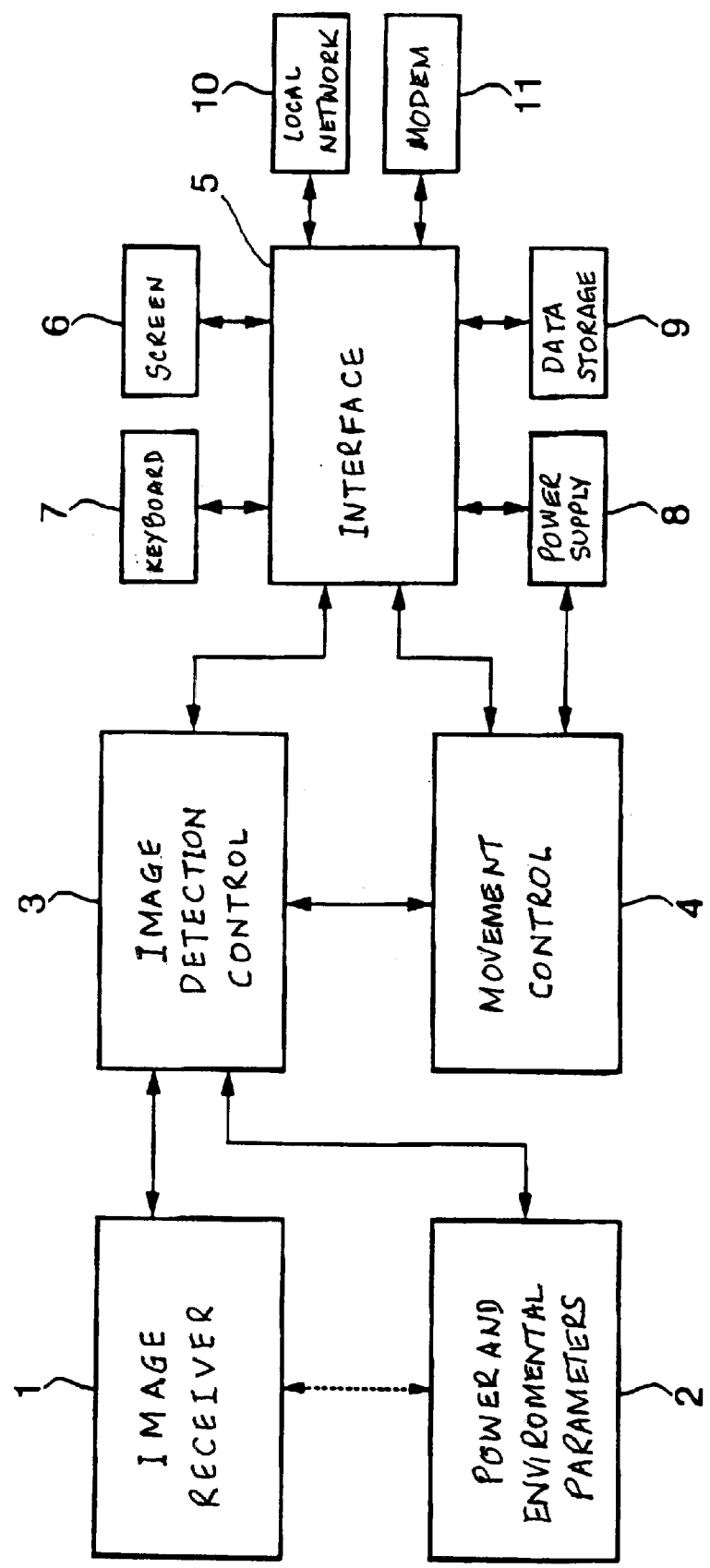
FIG. 1 is a schematic view of the different parts of an X-ray apparatus.

As can be seen on FIG. 1, the system contains an image receiver 1, for example, of solid state type, a unit 2 detecting the power and environment parameters, such as high voltage, supply current, exposure time, outside temperature, etc., and an image detection control unit 3 which takes charge of reading of the image receiver 1 and of image processing. That unit can contain a Pentium® type processor. The system further contains a movement control unit 4 in charge of the displacement in space of the different components of the apparatus as a function of the axes of rotation and translation with which it is provided, an interface 5, for example, a Unix® work station, which handles preparation and forming of the image for display and is connected to a screen 6 and a keyboard 7 available to the user.

An uninterruptible power supply unit 8 is connected to the interface 5 and to the displacement unit 4. A means of data storage 9, on CD-ROM, for example, is also connected to the interface 5. A local network 10 transfers data, for example, to other computers not represented. A modem 11 is connected to the interface 5 and makes possible the remote comnunication of data over an Internet type network and notably with a remote computer not represented, making monitoring and maintenance of the X-ray apparatus possible. That computer receives the data in html format and is equipped with a graphics interface enabling them to be displayed in user-friendly form.

Figure 2:
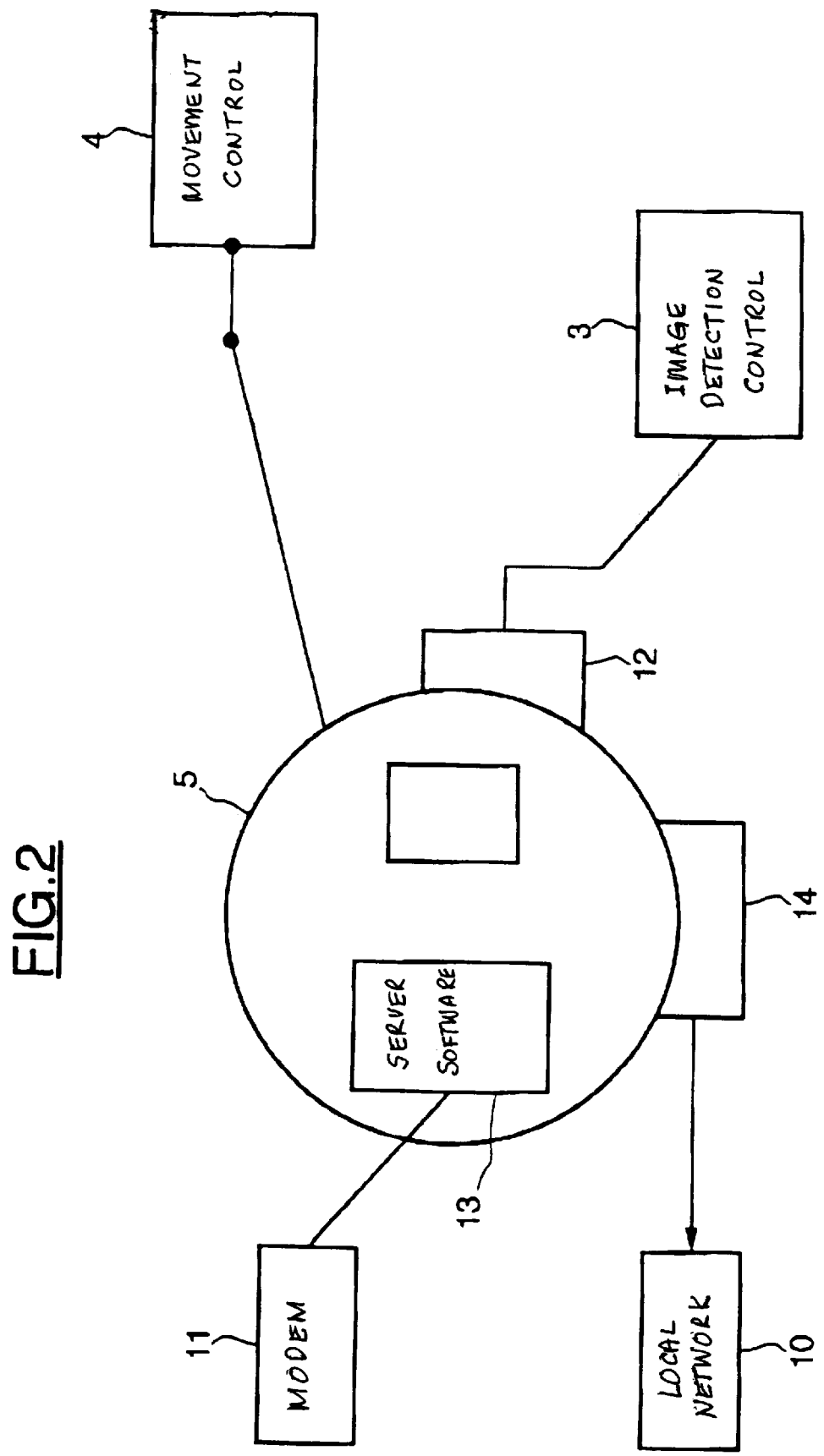
FIG. 2 is a more detailed schematic view of FIG. 1.

As can be seen, in particular, on FIG. 2, the interface 5 is provided with two server software packages referenced 12 and 13 and permitting communication over a Web type Internet system. Server software 12 is associated with the control unit 3. Server software 13 is associated with the interface 5 and is intended for transfer of data in html format with an Internet system through the modem 11. The link between the interface 5 and the displacement unit 4 is secured by a serial interface of RS 232 type, for example, which presents a very high flow. The data coming from the displacement unit 4 is put into html format by server software 12. Data transfer between the control unit 3 and the interface 5 is secured by server software 12, which can transfer data with the modem 11 through server software 13, but without the latter processing that data. In other words, the interface 5 is transparent to data transferred between the modem 11 and the control unit 3. Software 14 is intended for data transfer with the system 10. Software 14 makes it possible to limit access from an outside computer through the modem 11 to the internal system 10 of the hospital provided with a single address.

The independence of the interface 5 and control unit 3 involving communications over the Internet system makes possible a very simple software design. The presence of a communication protocol between the interface 5 and the control unit 3 is unnecessary insofar as the interface 5 does not have to understand or interpret the data passing through it between the modem 11 and the control unit 3. Thus, on the transmission of html pages by the control unit 3, no interpretation is made by the interface 5, which acts invisibly like an access provider.

Figure 3:
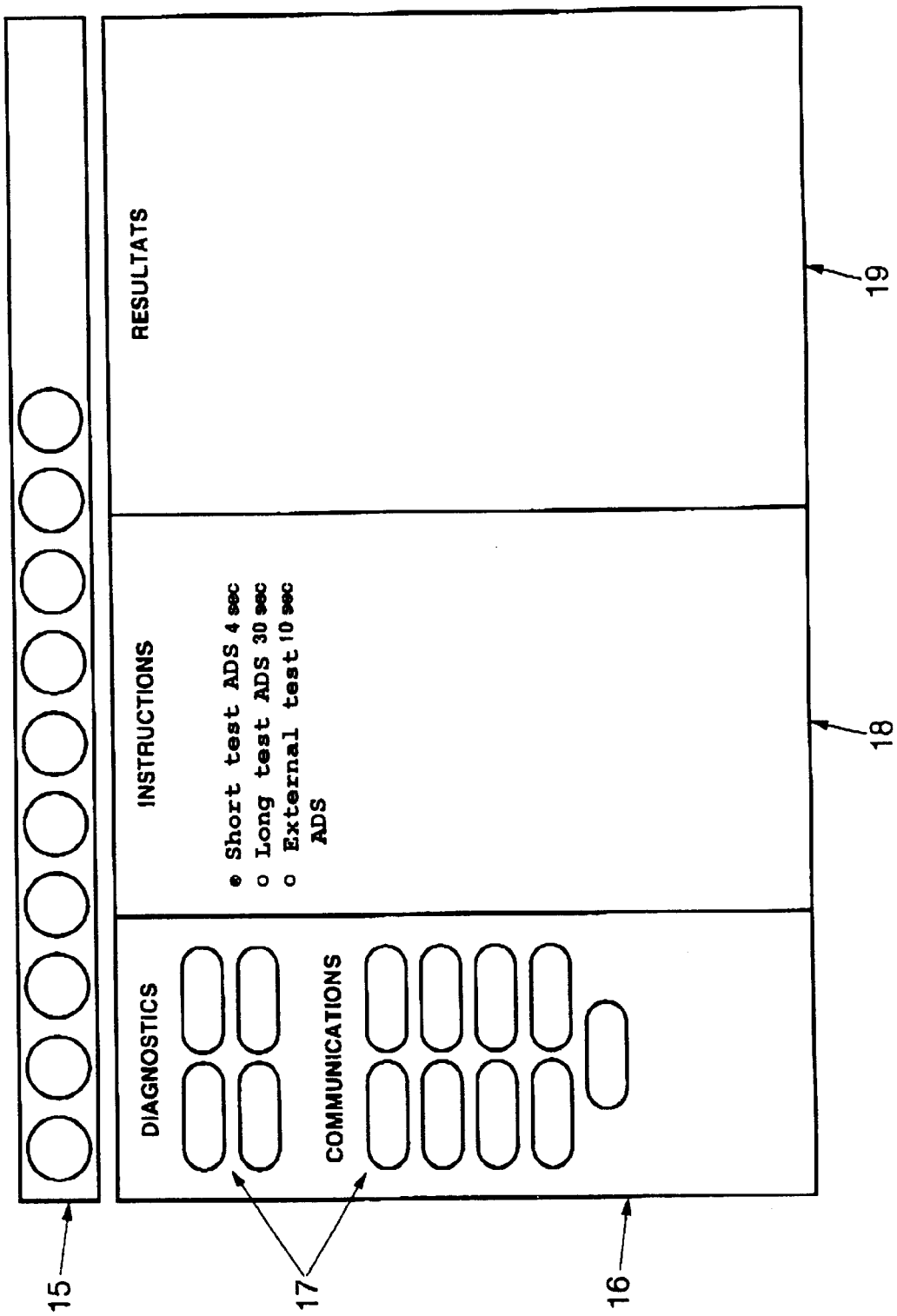
FIG. 3 is an example of a Web page provided with hypertext links used for maintenance.

In order to carry out maintenance operations, a number of Web pages are displayed on the screen 6 associated with the X-ray apparatus as well as on the screen of a remote computer situated, notably, at an on-line maintenance center of the manufacturer of the X-ray apparatus. An example of such a Web page is illustrated on FIG. 3. At the top 15 of the Web page a number of icons appear, corresponding to navigation software commands, such as close, print page displayed, zoom, etc. In the lower left part 16 of the Web page several hypertext links 17 appear under the "diagnostics" and "communications" chapter headings, making possible direct access to other documents. A diagnosis of the control unit 3, displacement unit 4, interface 5 or even of power supply means 8 can thus be launched. It is also possible to test communications between these different elements, notably, between the control unit 3 and the image receiver 1, between the control unit 3 and the detection unit 2, between the control unit 3 and the displacement unit 4, between the interface 5 and the displacement unit 4, between the interface 5 and the control unit 3, between the interface 5 and the supply means 8, between the interface 5 and the network 10 and between the interface 5 and the modem 11. In the lower center part 18 of the Web page, under the title "instructions," it is possible to choose different types of tests it should be desired to carry out and to start off these tests by clicking the "start" command. In the lower right part 19 of the Web page the results of the diagnosis made are displayed.

Figure 4:
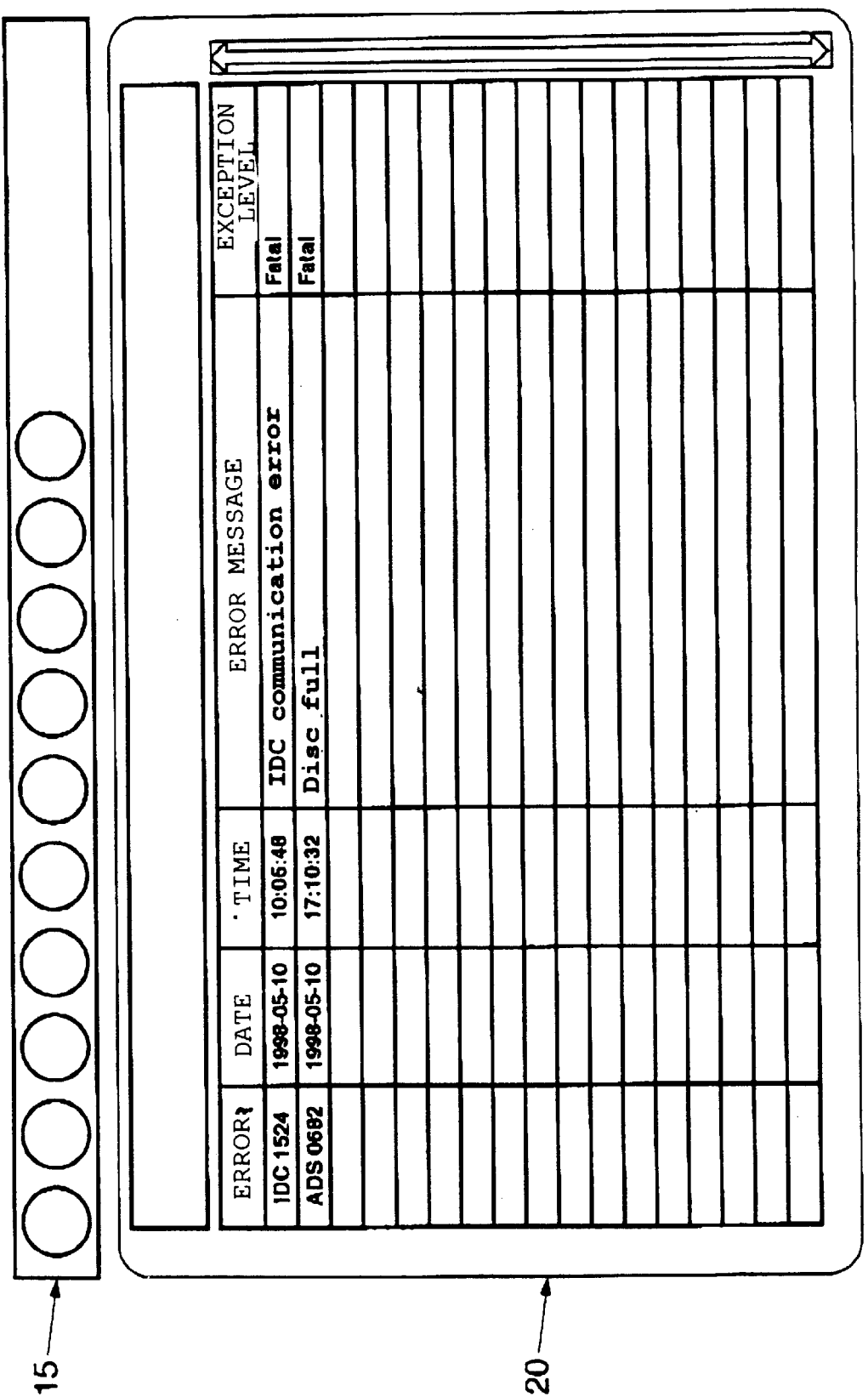
FIG. 4 is an example of a Web page displaying the list of errors having occurred in the X-ray apparatus.

The Web page illustrated on FIG. 4 makes it possible to display information relating to the errors detected and which are stored in a memory of the X-ray apparatus. This Web page contains an upper part 15 identical to that of the Web page illustrated on FIG. 3 and a lower part 20 that comes in the form of a table with columns. The first column shows identifiers of the errors stored, the second column shows the dates, the third column shows the hours, minutes and seconds at which the errors occurred, the fourth column shows the error messages containing clear indications of the nature of the errors that occurred, and the fifth column shows the levels of gravity of the different errors that occurred. The identifiers of the errors displayed in the first column constitute hypertext links by which detailed documentation on the nature of the errors and the means of correcting them can be accessed. That documentation is stored at the same time in a memory of the X-ray apparatus so that it can be displayed on the screen 6 and in a memory of the on-line maintenance center.

Thus, the only data having to be transferred by the modem 11 and the Internet system are the identifier of the error and the time at which it occurred. User-friendly on-line maintenance can thus be carried out with easy-to-use graphics interfaces, while having a relatively small quantity of data to be transferred by the on-line maintenance center and the X-ray apparatus.

The same is true for the different tests that an operator can control from an on-line maintenance center and which are provided with an identifier that is transferred by the Internet system, while all of the data relating to the tests is stored at the same time in a memory of the X-ray apparatus and at the on-line maintenance center and does not undergo transfer.

Each type of error is provided with a unique identifier or error code. When an error provided with a given identifier can have several possible causes, a tree of possible causes is then stored at the same time in a memory of the X-ray apparatus and in a memory of the on-line maintenance center, so as to be able to control all the remote tests and, in case of necessary replacement of a part, such as an electronic card of the X-ray apparatus, to send a technician with only the part to be replaced. The tree of possible causes of errors makes it possible to carry out automatic sequences of several tests in order to identify the real cause of the error very quickly and thus select the part that actually has to be replaced among all those likely to be involved when an error has several possible causes.

The error diagnostics is carried out by analysis of failure modes and of their critical nature from a model of the X-ray apparatus containing functional blocks. The assumption is made that a given block only emits the signal it has to emit. The probability of occurrence of such an event and the risk or nuisance it causes the user is estimated. It is then provided that high probability and high nuisance errors must systematically undergo a diagnosis, the low probability and low nuisance errors do not have to undergo a diagnosis and the low probability and high nuisance or high probability and low nuisance errors should undergo a diagnosis if the diagnosis is easy; in other words, if use of the diagnostic function does not present too many difficulties.

Thus, a technician at an on-line maintenance center can display the list of errors memorized in the X-ray apparatus, display a diagnosis established according to the error or errors, make a calibration, modify the configuration of parameters in case of change of desiderata, or even measure the quality of the remote image. If it should prove necessary to replace a component or component part of the X-ray apparatus, the technician travels only once after having made a diagnosis and procured the component or component part to be replaced. A substantial reduction of maintenance cost of X-ray apparatuses is thus accomplished.

In order to make that remote link, an Internet type communication network is used, preferably provided with access protection means. It is to be pointed out here that the Internet is a network essentially comprising telephone lines connected to computer servers capable of communicating with other computer servers. A computer server is a computer system containing computer programs and consultable documents (texts, sounds, images) and can be connected by telephone lines to individual users, enabling them thus to join the network. The network user has to be equipped with a computer and modem connecting the computer to a telephone line and can thus consult a set of information in different domains.

A graphics interface is generally used, making it possible by simple pointing to access documents on the network containing text, static images, sounds and animated images as well as links.

Access to documents is made by using consulting software, also called "navigator," which manages the user's graphics interface and the links making it possible with a simple click of the computer mouse to access documents designated by the mouse pointer. The links enable passage from one document to another by using the hypertext link technique, which makes it possible, by clicking on a set of words displayed, for example, in a frame or shading, to load a new document on the user's navigator. The transition from one document to another can also be made by introducing the computer address of the document desired.

The Internet link thus makes possible the remote monitoring and maintenance of an X-ray apparatus.

The invention can be applied particularly well to wide-field digital X-ray apparatuses.

The disadvantages of the prior art are avoided, namely, the lack of user friendliness and poverty of graphics on transfer of ASCII files and too great a flow of data necessary on complete image transfer, which would lead to a very slow and costly operation. On the other hand, one benefits from pleasing Web pages to be used on the screen 6 of the X-ray apparatus as well as at the on-line maintenance center or on any computer connected thereto, which makes it possible to carry out maintenance operations quickly and to limit the travel of maintenance personnel strictly to operations of replacement of material parts of the X-ray apparatus.

Various modifications in structure and/or steps and/or function may be made by one skilled in the art without departing from the scope of the invention.

What is claimed is:

1. A radiology system comprising:
   means for emission of an X-ray beam;
   means for reception of the X-ray beam after it has crossed an organ to be studied;
   means for reception control;
   means for forming an image, the means for forming an image comprising a computer storing in memory a document relating to errors that can occur in the system, the computer being provided with a screen and a graphics interface and capable of displaying on the screen at least one page containing a list of errors having occurred in the system with hyperlinks to the document;
   a first network server associated with the means for reception control;
   a second network server associated with the means for forming an image; and
   means for providing a remote computer,
   each server being capable of transmitting data in html format to the means for providing a remote computer.

2. The system according to claim 1 wherein the means for providing a remote computer is capable of showing the page displayed by the means for providing a remote computer of the means for forming an image.

3. The system according to claim 1 wherein the means for providing a remote computer is capable of showing the page displayed by the means for providing a remote computer of the means for forming an image.

4. The system according to claim 1, wherein it includes at least one accessory connected to the means for forming an image and capable of transmitting to the means for providing a remote computer through the means for forming an image and the associated server.

5. The system according to claim 1, comprising means for diagnostic loaded with errors that can occur in the system, the means for diagnostic being capable of diagnosing given errors selected according to their occurrence probability, the trouble they are likely to cause the user and the difficulty of using the corresponding diagnosis.

6. The system according to claim 1, wherein the document contains, for each type of error, at least one test to be carried out to determine its cause.

7. The system according to claim 6 wherein the means for providing a remote computer is capable of showing the page displayed by the means for providing a remote computer of the means for forming an image.

8. The system according to claim 1, wherein the data in html format transmitted by the server associated with the means for reception control to the means for providing a remote computer pass through the means for forming an image and associated server.

9. The system according to claim 8, wherein the data only undergo the processing necessitated by the passage through the means for forming an image and associated server.

10. The system according to claim 1, wherein the means for providing a remote computer is capable of receiving data in html format from the servers, the means for providing a remote computer storing in memory a document relating to errors that can occur in the system and the means for providing a remote computer being provided with a screen and a graphics interface and capable of displaying on the screen at least one page containing a list of errors having occurred in the system with hyperlinks to the document.

11. The system according to claim 10 wherein the means for providing a remote computer is capable of showing the page displayed by the means for providing a remote computer of the means for forming an image.

12. The system according to claim 10, wherein the document contains, for each type of error, at least one test to be carried out to determine its cause.

13. The system according to claim 12 wherein the means for providing a remote computer is capable of showing the page displayed by the means for providing a remote computer of the means for forming an image.

14. Method of data transmission from an X-ray system comprising means for emission of an X-ray beam, means for reception of the X-ray beam after it has crossed an organ to be studied, means for reception control and means for forming an image, wherein the means for forming an image comprises a computer storing in memory a document relating to errors that can occur in the system, the computer being provided with a screen and a graphics interface; comprising:

transmitting data in html format to a remote computer from a first network server associated with the means for reception control, transmitting data in html format from a second network server associate with the means for forming an image, and displaying on the screen at least one page containing a list of errors having occurred in the system with hyperlinks to the document.

15. A radiology system comprising:

means for emission of a beam of radiation;

means for reception of the beam after it has crossed an object to be studied;

means for reception control;

means for forming an image;

means for storing errors that can occur in the system and displaying errors having occurred in the system with hyperlinks to the means for storing errors;

a first network server associated with the means for reception control;

a second network server associated with the means for forming an image; and means for providing a remote computer, each server being capable of transmitting data in html format to the means for providing a remote computer.

16. The system according to claim 15, comprising means for diagnostic loaded with errors that can occur in the system, the means for diagnostic being capable of diagnosing given errors selected according to their occurrence probability, the trouble they are likely to cause the user and the difficulty of using the corresponding diagnosis.

17. The system according to claim 15, wherein it includes at least one accessory connected to the means for forming an image and capable of transmitting to the means for providing a remote computer through the means for forming an image and the associated server.

18. The system according to claim 15 wherein the means for providing a remote computer storing in memory a document relating to errors that can occur in the system and the means for providing a remote computer being provided with a screen and a graphics interface and capable of displaying on the screen at least one page containing a list of errors having occurred in the system with hyperlinks to the document.

19. The system according to claim 15, wherein the data in html format transmitted by the server associated with the means for reception control to the means for providing a remote computer pass through the means for forming an image and associated server.

20. The system according to claim 19, wherein the data only undergo the processing necessitated by the passage through the means for forming an image and associated server.

21. The system according to claim 15, wherein the means for providing a remote computer is capable of receiving data in html format from the servers.

22. The system according to claim 21 wherein the means for providing a remote computer is capable of showing the page displayed by the means for providing a remote computer of the means for forming an image.

23. A method of data transmission from an system comprising means for emission of a beam of radiation, means for reception of the beam after it has crossed an object to be studied, means for reception control means for forming an image and means for storing in memory errors that can occur in the system comprising:

transmitting data in html format to a remote computer from a first network server associated with the means for reception control;

transmitting data in html format from a second network server associate with the means for forming an image;

displaying errors having occurred in the system with hyperlinks to the means for storing in memory; and each server being capable of transmitting data in html format to the remote computer.

24. The method according to claim 23 wherein the system includes means loaded with errors that can occur in the system, and wherein the errors are selected according to their occurrence probability, the trouble they are likely to cause the user and the difficulty of using a corresponding diagnosis for identifying and correcting the errors.

25. The method according to claim 23 wherein the remote computer is capable of receiving data in html format from the servers, the remote computer is capable of displaying errors that have occurred in the system with hyperlinks to the means for storing in memory.

26. The method according to claim 23 wherein the data in html format transmitted by the server associated with the means for reception control to the remote computer pass through the means for forming an image and associated server.

27. The method according to claim 26 wherein the data only undergo the processing necessitated by the passage through the means for forming an image and associated server.

28. The method according to claim 23 wherein the means for storing includes a document relating to errors that can occur in the system and wherein the displaying includes at least one page containing a list of errors having occurred in the system.

29. The method according to claim 8 wherein the document contains, for each type of error, at least one test to be carried out to determine the cause of the error.

30. The method according to claim 28 wherein the remote computer is capable of showing the page.

* * * * *